United States Patent
Broselow

(10) Patent No.: US 6,764,469 B2
(45) Date of Patent: Jul. 20, 2004

(54) COLOR-CODED MEDICAL DOSING CONTAINER

(76) Inventor: James B. Broselow, 1315 Wessex La., Hickory, NC (US) 28602

(*) Notice: Subject to any disclaimer, the term of this patent is extended or adjusted under 35 U.S.C. 154(b) by 118 days.

(21) Appl. No.: 10/210,992

(22) Filed: Aug. 2, 2002

(65) Prior Publication Data

US 2004/0024368 A1 Feb. 5, 2004

(51) Int. Cl.[7] .......................... A61M 5/00; A61M 5/315
(52) U.S. Cl. ..................... 604/207; 604/211; 604/222
(58) Field of Search .................... 604/211–222, 187, 604/208–206, 194, 209, 900, 210, 186, 506, 207

(56) References Cited

U.S. PATENT DOCUMENTS 4,153,056 A * 5/1979 Silver et al. ............... 604/211
5,376,081 A * 12/1994 Sapienza .................... 604/207
6,132,416 A * 10/2000 Broselow ................... 604/506

* cited by examiner

Primary Examiner—Brian L. Casler
Assistant Examiner—Roz Ghafoorian
(74) Attorney, Agent, or Firm—Adams Evans P.A.

(57) ABSTRACT

A syringe including a barrel for retaining fluid and having a dispensing port for permitting fluid flow therethrough. A plunger is received within the barrel and is axially moveable relative thereto for controlling fluid flow through the dispensing port. A dosing indicator is carried by the plunger and includes indicia thereon collectively representing a dosing range of the fluid based upon a correlation between the indicia and a therapeutic treatment variable for a preselected group of patients. The indicia cooperate with the plunger and barrel for measuring a medically correct dose of the fluid to be administered to a patient from the group.

18 Claims, 13 Drawing Sheets

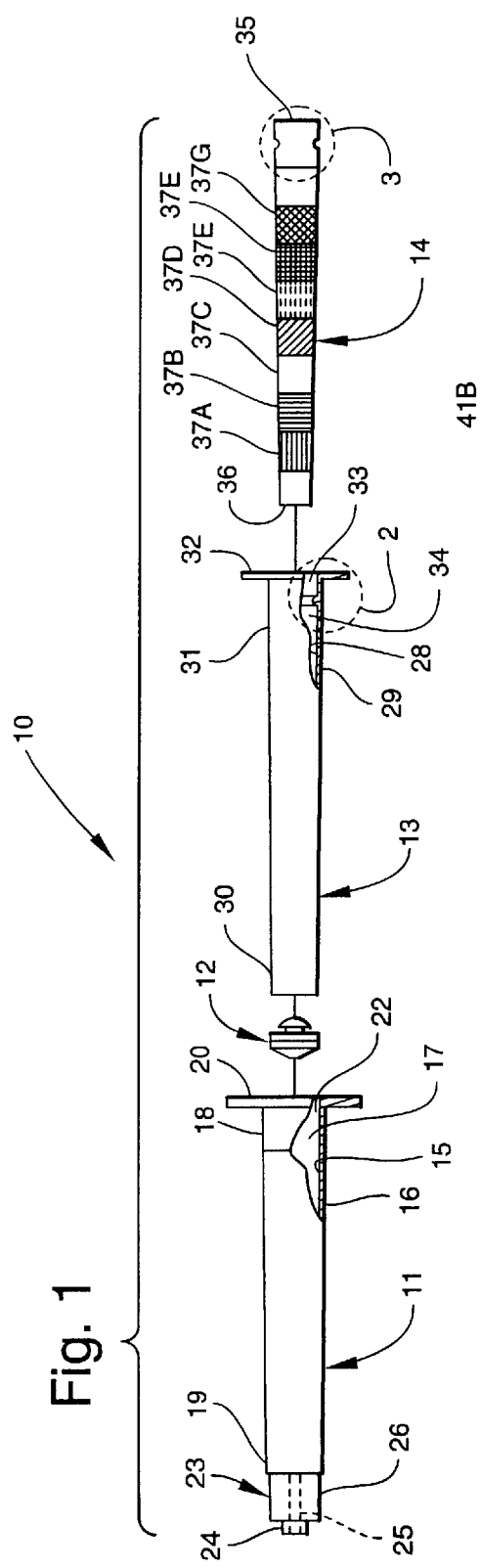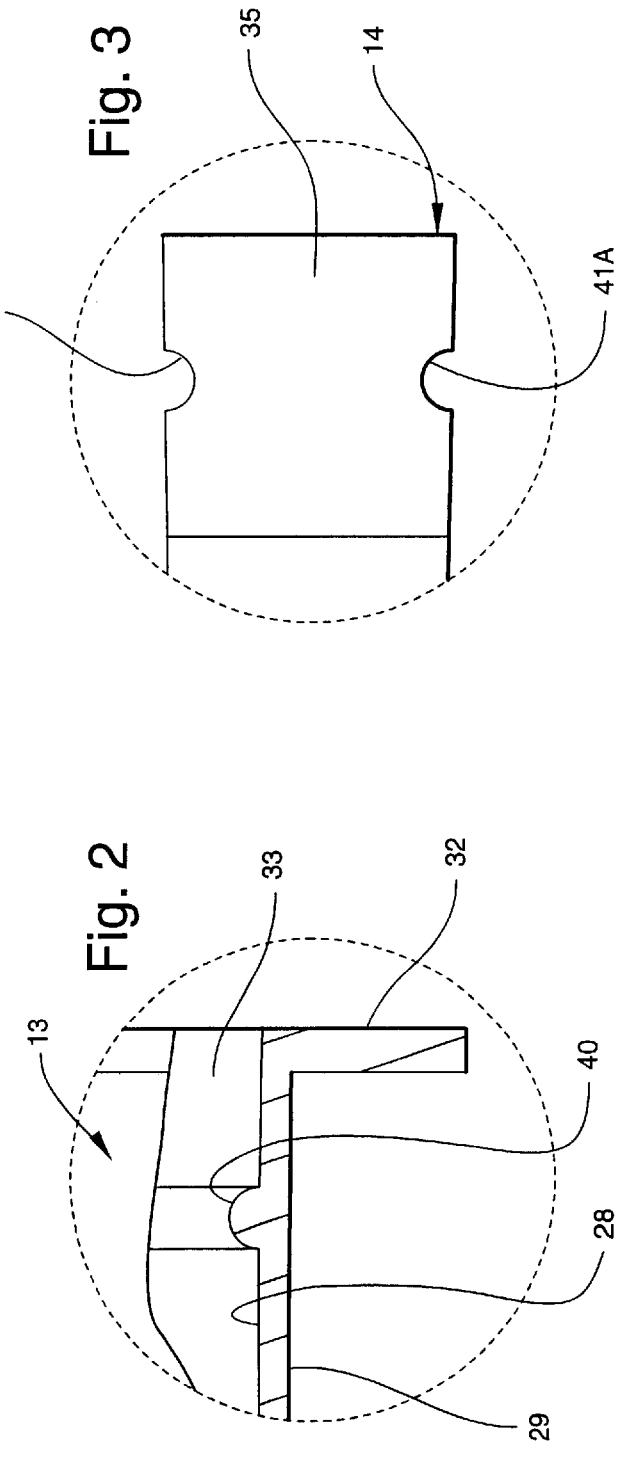

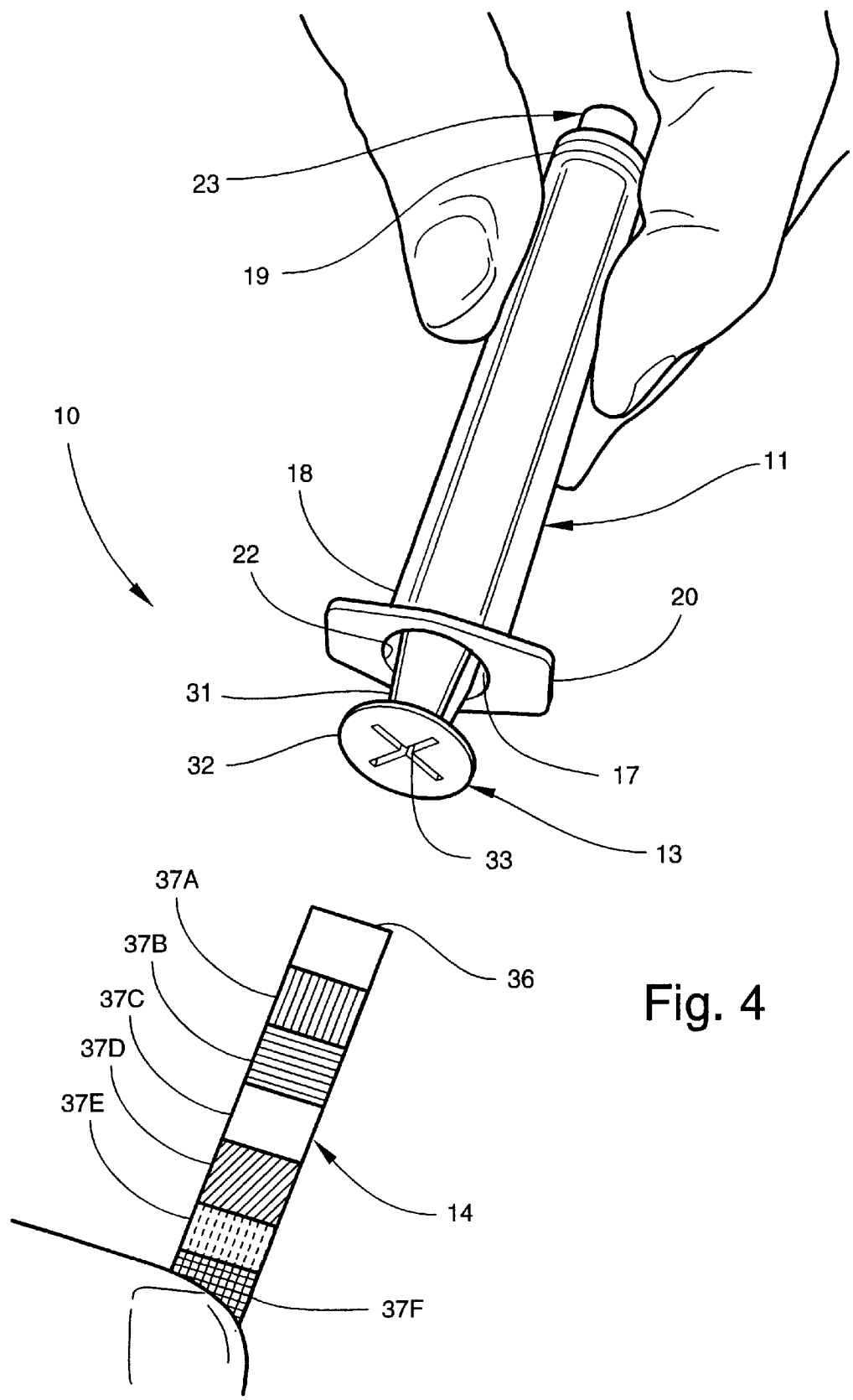

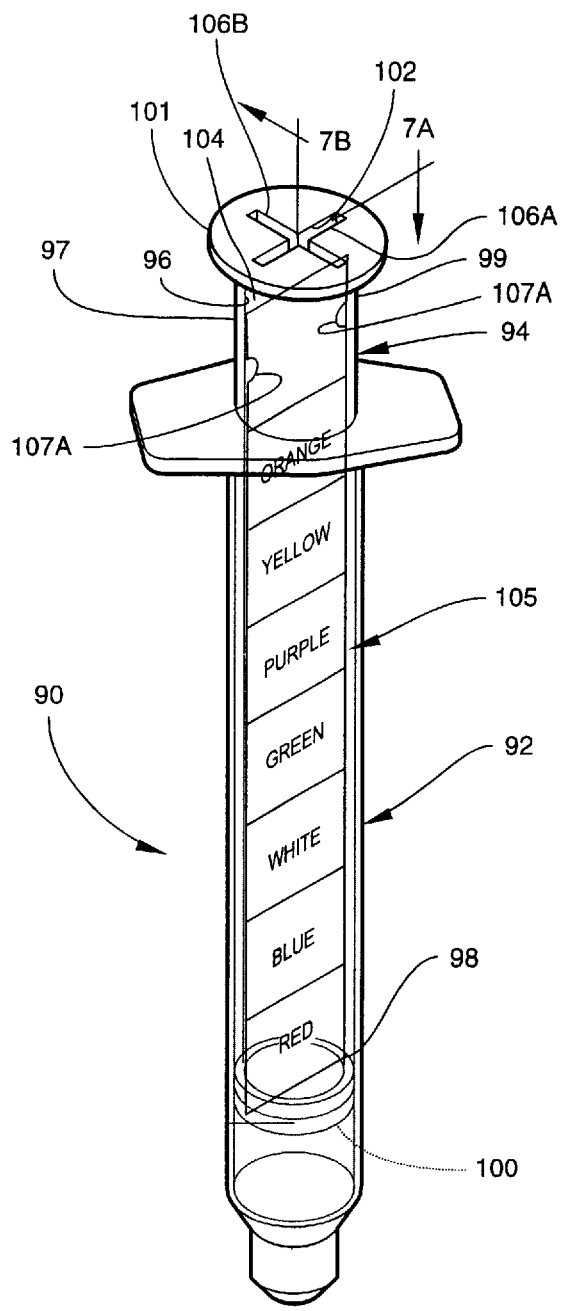
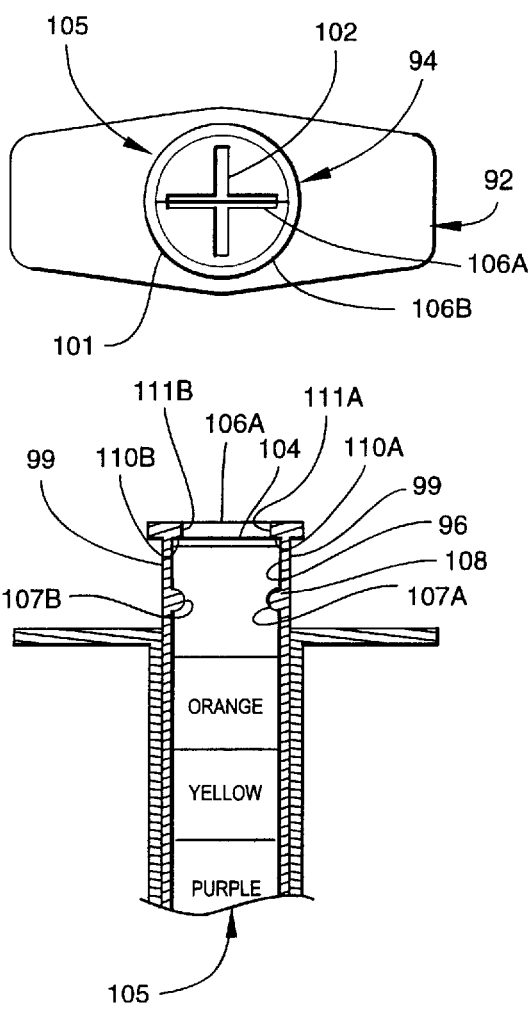
Fig. 7
Fig. 7A
Fig. 7B

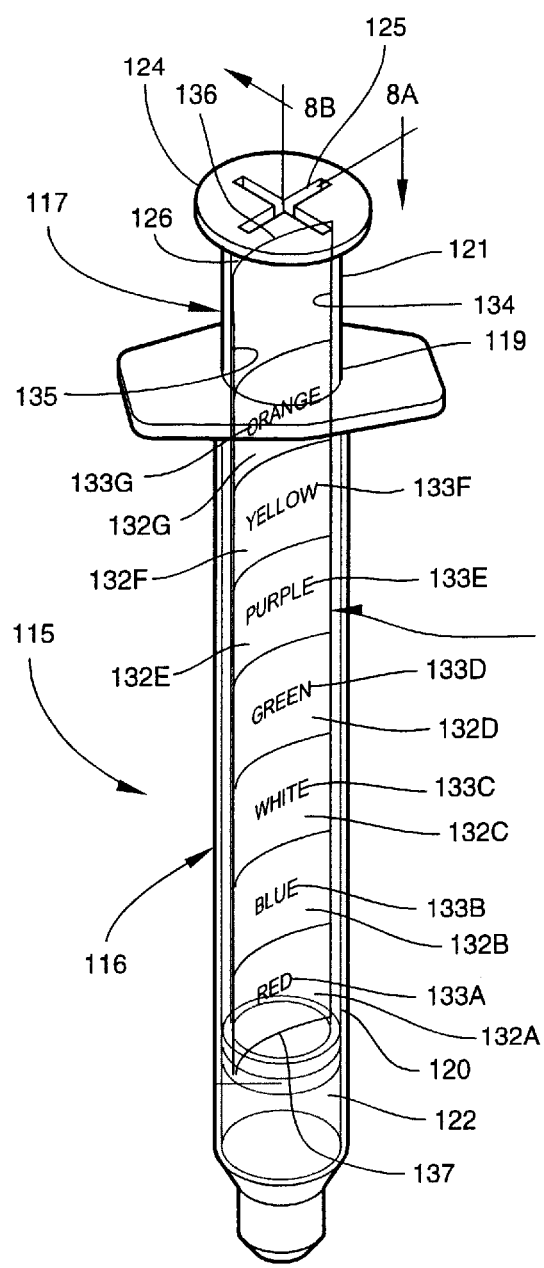
Fig. 8
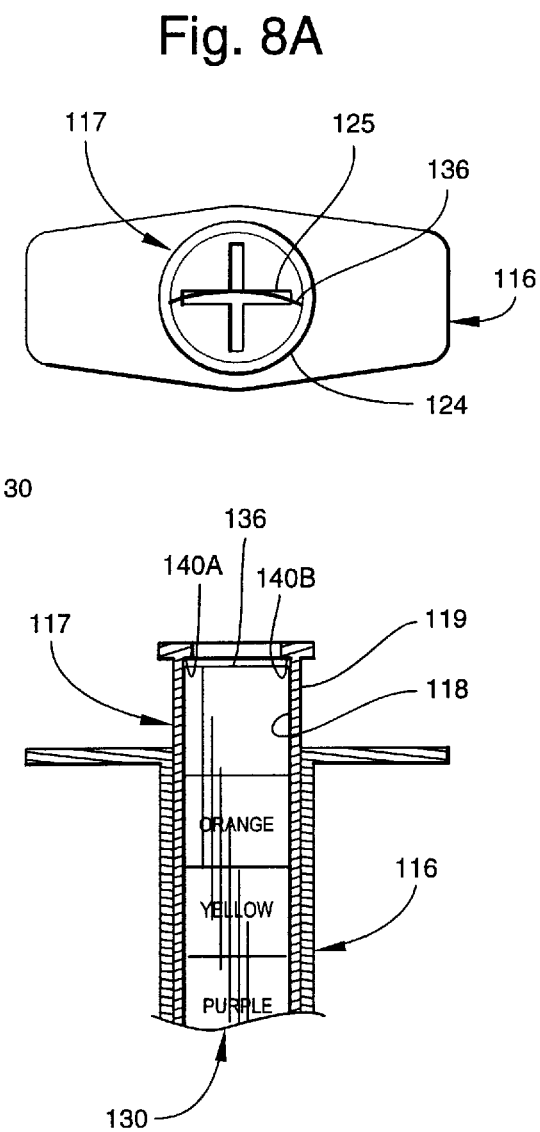
Fig. 8A
Fig. 8B

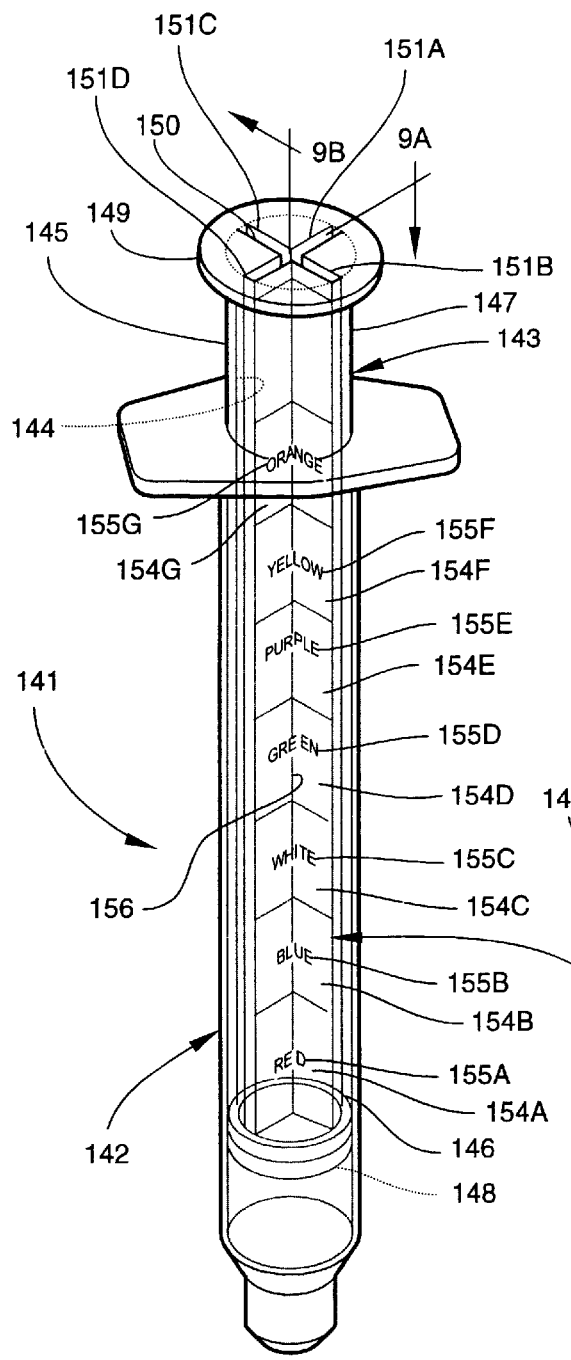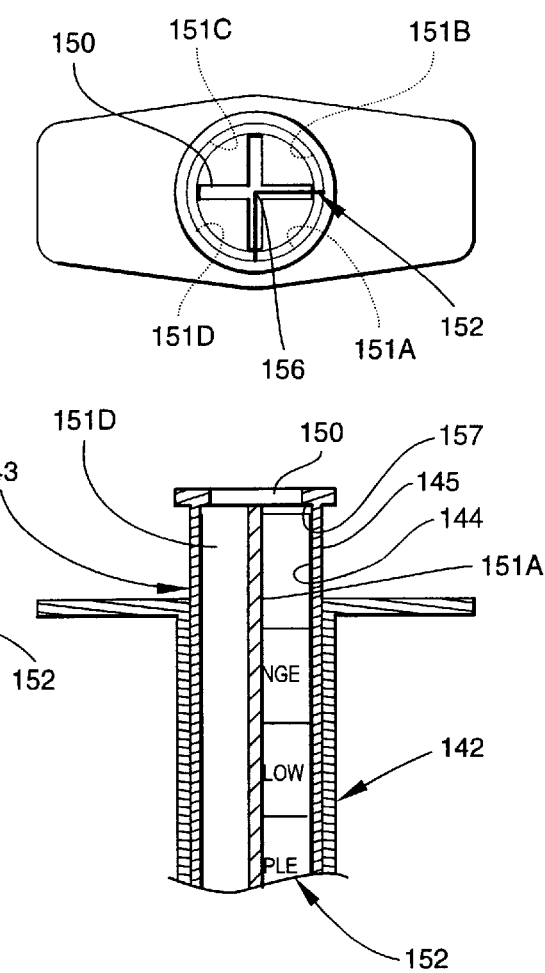
Fig. 9
Fig. 9A
Fig. 9B

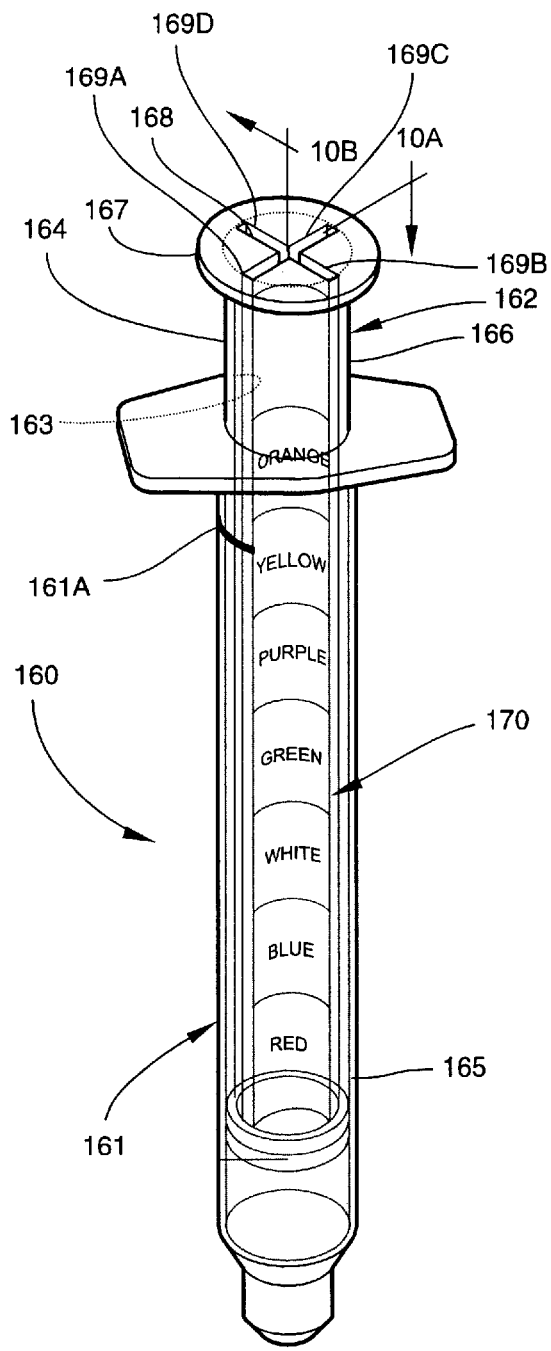
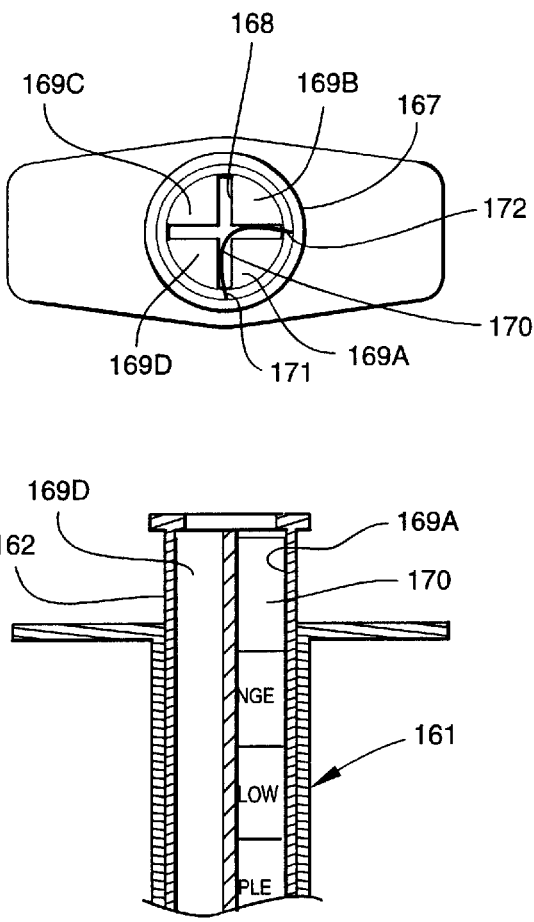
Fig. 10
Fig. 10A
Fig. 10B

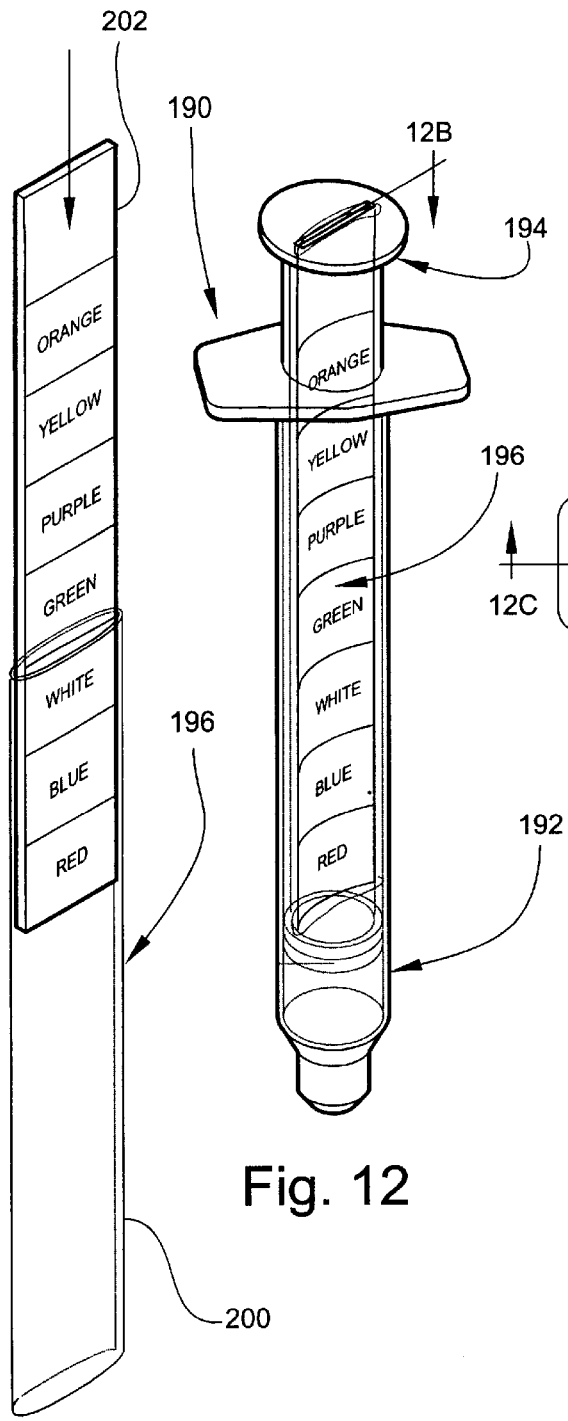
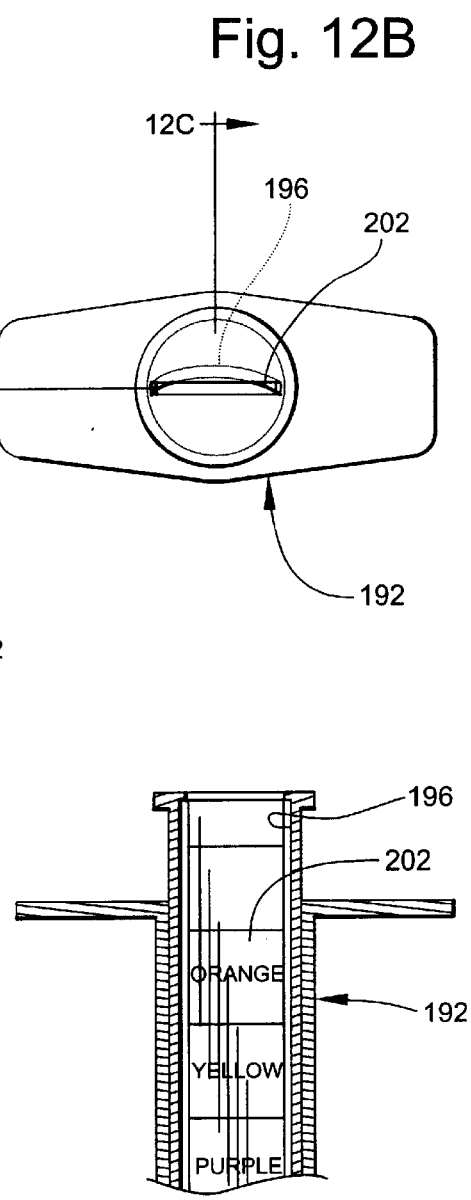
Fig. 12A
Fig. 12
Fig. 12B
Fig. 12C

COLOR-CODED MEDICAL DOSING CONTAINER

TECHNICAL FIELD AND BACKGROUND OF THE INVENTION

This invention relates to a color-coded medical dosing container designed to simplify, expedite and increase the accuracy of medication dosing for patients. The particular embodiments disclosed herein are of a syringe that utilizes interchangeable dosing inserts which are removably positioned within a plunger. Each dosing insert features a series of color-coded dosing zones based on a universal dosing value of the patient, such as weight or length. The universal dosing value is used to assign a dosing zone, or "color", to the patient. Once the proper dosing "color" has been assigned, the color is used to determine correct doses of medication for the patient. The assigned color remains the same for all medication dosing as long as the weight or length of the patient remains within the range of lengths or weights that fall within the dosing zone to which the assigned color applies.

Although the syringe of the present invention has application in any clinical, public or home health setting where providing accurate doses of medication is required, the invention is specifically intended for use in providing care to pediatric patients. As used herein, medication may include, but is not limited to, any prescription or non-prescription fluid for treating a medical condition or for providing nutrition or hydration to a patient or other individual.

Color-coded dosing zones are utilized as part of a universal medication dosing system, as disclosed in U.S. Pat. Nos. 4,713,888 and 6,132,416. However, those patents fail to address problems associated with using a syringe to measure and administer medications. Prior methods of using a syringe to administer doses of medication involve using a plunger to draw the medication into the barrel of the syringe while simultaneously attempting to determine the volume of medication in the barrel by reading a dosing scale which is printed on the outside of the barrel. A measurement of the volume of fluid in the barrel can only be made by viewing gradations on the outside of the barrel.

The risk of error associated with prior art syringes is further exacerbated by the likelihood that the dosage amount was either determined by making an educated guess or quickly performing a multi-step mathematical calculation in an attempt to convert a given concentration of the medication in question to arrive at a dose appropriate for the patient. Even under the best of circumstances, inadvertent mistakes are sometimes made when calculating doses of medicine—especially when a pediatric patient is involved. While such risks are present when determining doses for adults, they are more critical in determining doses for pediatric patients. Unfortunately, providing a dosing method that eliminates the need for such calculations does not adequately address the disadvantages associated with using a prior art syringe to deliver a dose of medication to a patient. Regardless of whether the dose is determined using a color-coded or other simplified dosing scale, the position of the scale on the outside of the barrel of the syringe limits the number of medications for which the syringe may be used to those medications sharing a common concentration. This decreases the cost-effectiveness of the syringe by reducing the ways in which the syringe may be utilized to deliver medication to the patient.

The present invention addresses the problems associated with prior art methods of determining and administering medically correct doses of fluid or drugs to a patient by providing a syringe having a plunger within which a removable color-coded insert is positioned. The insert includes a series of color-coded or similarly designated dosing zones along its length. The position of each zone relative to the stopper on the plunger is inversely correlated to the volume of fluid retained within the interior of the barrel. Therefore, dosing zones appearing on the insert near the proximal end of the plunger adjacent the handle are used to measure smaller volumes of fluid within the barrel of the syringe and correspond to smaller doses of fluid. In contrast, zones appearing on the insert near the distal end of the plunger close to the stopper are used to measure larger volumes of fluid and correspond to larger doses.

Positioning the zones on the insert and orienting the insert inside the plunger of the syringe of the present invention eliminates the need to remove the syringe from the dosing container to read the volume of fluid present in the barrel or on the plunger. Rather than bringing the syringe to eye level, the dose amount is determined by aligning the dosing zone assigned to the patient with a flange or other reference mark located on the barrel. Provided that the healthcare provider correctly assigns and recalls the "color" of the patient, and then positions the plunger so that the dosing zone corresponding to that color is aligned with the reference line or flange on the barrel, the proper dose will be drawn into the barrel. Given the tremendous number of circumstances in which syringes are used to measure the correct dose of a medication and then accurately administer that dose to pediatric patients or other children, the present invention provides an effective way of enhancing the accuracy, reliability, cost-effectiveness and speed with which medical care may be provided.

SUMMARY OF THE INVENTION

Therefore, it is an object of the invention to provide a dosing syringe that reduces the amount of time required to determine and administer a dose of medication to a patient while simultaneously decreasing the risk that such dose will be miscalculated or otherwise erroneously administered.

It is another object of the present invention to provide a dosing syringe that offers a cost-effective and expeditious method of administering doses of medication or other fluids to a patient.

It is another object of the present invention to provide a dosing syringe that correlates preselected physiological values indicative of a range of medically-correct dosages with a predetermined range of colors or other indicia.

It is another object of the present invention to provide a dosing syringe that eliminates the need to perform a multi-step mathematical calculation to arrive at a correct dose of medication for a pediatric patient.

It is another object of the invention to provide a dosing syringe having a color-coded dosing scale carried by the plunger instead of the barrel, which permits the quantity of medication being drawn into the syringe to be accurately measured and read without requiring that the tip of the syringe be removed from the container from which the medication is being withdrawn, and without otherwise obscuring visual access to the dosing scale.

These and other objects of the present invention are achieved in the preferred embodiments described below by providing a dosing syringe with a barrel defining a chamber therein for retaining fluid and including a dispensing port communicating with the chamber for permitting fluid flow therethrough. The dosing syringe includes a plunger for being matingly received within the chamber. The plunger is axially moveable relative to the barrel for controlling fluid flow through the dispensing port. A dosing indicator is removably carried by the plunger and includes indicia thereon collectively representing a dosing range of the fluid based upon a correlation between the indicia and a therapeutic treatment variable for a preselected group of patients. The indicia cooperate with the plunger and barrel for measuring a medically correct dose of the fluid to be administered to a patient from the group.

According to one preferred embodiment of the invention, the dosing indicator is removably positioned within the plunger for permitting alternative uses of the syringe.

According to another preferred embodiment of the invention, the indicia comprise preselected strips of color arranged in a fixed sequence on the dosing indicator.

According to yet another preferred embodiment of the invention, each of the indicia is a respective one of a series of chevrons positioned in spaced-apart relation along the length of the dosing indicator.

According to yet another preferred embodiment of the invention, the indicia are preselected words arranged in a fixed sequence on the dosing indicator.

According to yet another preferred embodiment of the invention, each of the words corresponds to a preselected color for permitting a color-blind individual to use the syringe.

According to yet another preferred embodiment of the invention, each of the strips of color is overlaid by a respective one of a series of reference marks.

According to yet another preferred embodiment of the invention, the barrel includes a proximal opening communicating with the chamber for receiving the plunger therein.

According to yet another preferred embodiment of the invention, the plunger includes a first end for being matingly received within the proximal opening of the barrel, and a second end for manipulating axial movement of the plunger relative to the barrel.

According to yet another preferred embodiment of the invention, the syringe includes an interior compartment defined by the plunger and adapted for receiving the dosing indicator therein.

According to yet another preferred embodiment of the invention, the interior compartment is concentrically positioned within the plunger and communicates with a complementary opening defined by and extending through the second end of the plunger.

According to yet another preferred embodiment of the invention, the interior compartment is an elongate slot.

According to yet another preferred embodiment of the invention, the slot includes two integrally formed, elongate segments positioned perpendicularly to one another and extending parallel to the longitudinal axis of the plunger.

According to yet another preferred embodiment of the invention, the segments intersect with each other to form an X-shaped cross section extending perpendicularly to the longitudinal axis of the plunger.

According to yet another preferred embodiment of the invention, an alignment indicator is carried by the barrel for being aligned with a preselected one of the indicia on the dosing indicator, thereby permitting the medically correct dose of the fluid to be measured prior to administering the dose to the member of the preselected patient population.

According to yet another preferred embodiment of the invention,the dosing indicator comprises an elongate insert having a shape complementary to a cross-sectional segment of said slot.

According to yet another preferred embodiment of the invention, the interior compartment includes a plurality of equally-spaced channels defined by and extending along the length of the plunger. Each of the channels is adapted for receiving the dosing indicator therein.

According to yet another preferred embodiment of the invention, the dosing indicator is an elongate insert.

According to yet another preferred embodiment of the invention, the insert includes a fold extending parallel to the longitudinal axis thereof for maintaining the insert in a stationary position within a preselected one of the channels.

According to yet another preferred embodiment of the invention, the insert is a flexible strip for being placed in a bent position within a preselected one of the channels, thereby maintaining the strip in a stationary position with the channel.

According to yet another preferred embodiment of the invention, the dosing indicator is carried on an exterior sidewall of the plunger for permitting ease of assembly and use of the syringe.

According to yet another preferred embodiment of the invention, a dosing syringe is provided that includes a barrel defining a chamber therein for retaining fluid. The barrel has a dispensing port and a proximal opening communicating with the chamber for permitting fluid flow therethrough. A plunger is matingly received within the chamber through the proximal opening and is axially moveable relative to the barrel for controlling fluid flow through the dispensing port. A dosing indicator is removably positioned within a compartment defined by the plunger. The dosing indicator includes indicia thereon collectively representing a preselected series of colors corresponding to a dosing range of the fluid based upon a correlation between the indicia and a therapeutic treatment variable for a preselected group of patients. The indicia cooperate with the plunger and the barrel for measuring a medically correct dose of the fluid to be administered to a patient from the group.

According to a preferred embodiment of a method for practicing the invention, a method of measuring a medically correct dose of fluid for being administered to a patient is provided. The method includes the step of providing a dosing syringe. The syringe includes a barrel defining a chamber therein for retaining fluid. The barrel has a dispensing port and a proximal opening communicating with the chamber for permitting fluid flow therethrough. A plunger is matingly received within the chamber through the proximal opening and is axially moveable relative to the barrel for controlling fluid flow through the dispensing port. A dosing indicator is removably carried by the plunger and includes indicia thereon collectively representing a dosing range of the fluid based upon a correlation between the indicia and a therapeutic treatment variable for a preselected group of patients. The indicia cooperate with the plunger and barrel for measuring a medically correct dose of the fluid to be administered to a patient from the group. A predetermined one of the indicia is assigned to the patient using the therapeutic treatment variable. A container of the fluid is provided, and the dispensing end of the barrel is immersed in the fluid. The plunger is used to withdraw the fluid from the container and into the chamber until the predetermined indicia is aligned with a reference mark on the barrel, thereby indicating the medically correct dose of fluid is in the chamber.

BRIEF DESCRIPTION OF THE DRAWINGS

Some of the objects of the invention have been set forth above. Other objects and advantages of the invention will appear as the invention proceeds when taken in conjunction with the following drawings, in which:

FIG. 1 is an exploded plan view of a dosing syringe according to one preferred embodiment of the invention;

FIG. 2 is a partial cross-sectional view of the second end of the plunger of the syringe according to FIG. 1;

FIG. 3 is a partial cross-sectional view of the proximal end of the dose measurement indicator of the syringe according to FIG. 1;

FIG. 4 is an environmental perspective view of the syringe illustrating the manner in which the dose measurement indicator is positioned within the plunger;

FIGS. 6A through 6D are front plan views of respective dose measurement indicators for use in dosing syringes according to alternative embodiments of the invention;

FIG. 7 is a perspective view of a dosing syringe according to an alternative embodiment of the invention;

FIG. 7A is a top plan view of the dosing syringe taken along Line 7A of FIG. 7;

FIG. 7B is a partial cross-sectional side view of the dosing syringe taken along Line 7B of FIG. 7;

FIG. 8 is a perspective view of a dosing syringe according to an alternative of the invention;

FIG. 8A is a top plan view of the dosing syringe taken along Line 8A of FIG. 8;

FIG. 8B is a partial cross-sectional side view of the dosing syringe taken along Line 8B of FIG. 8;

FIG. 9 is a perspective view of a dosing syringe according to an alternative embodiment of the invention;

FIG. 9A is a top plan view of the dosing syringe taken along Line 9A of FIG. 9;

FIG. 9B is a partial cross-sectional side view of the dosing syringe taken along Line 9B of FIG. 9;

FIG. 10 is a perspective view of a dosing syringe according to an alternative embodiment of the invention;

FIG. 10A is a top plan view of the dosing syringe taken along Line 10A of FIG. 10;

FIG. 10B is a partial cross-sectional side view of the dosing syringe taken along Line 10B of FIG. 10;

FIG. 12 is a perspective view of a dose measurement indicator according to an alternative embodiment of the invention;

FIG. 12A is a perspective view of a dosing syringe according to an alternative embodiment of the invention;

FIG. 12B is a top plan view of the dosing syringe taken along Line 12B of FIG. 12A;

FIG. 12C is a partial cross-sectional side view of the dosing syringe taken along Line 12C of FIG. 12B;

DETAILED DESCRIPTION OF THE PREFERRED EMBODIMENT AND BEST MODE

Figure 5:
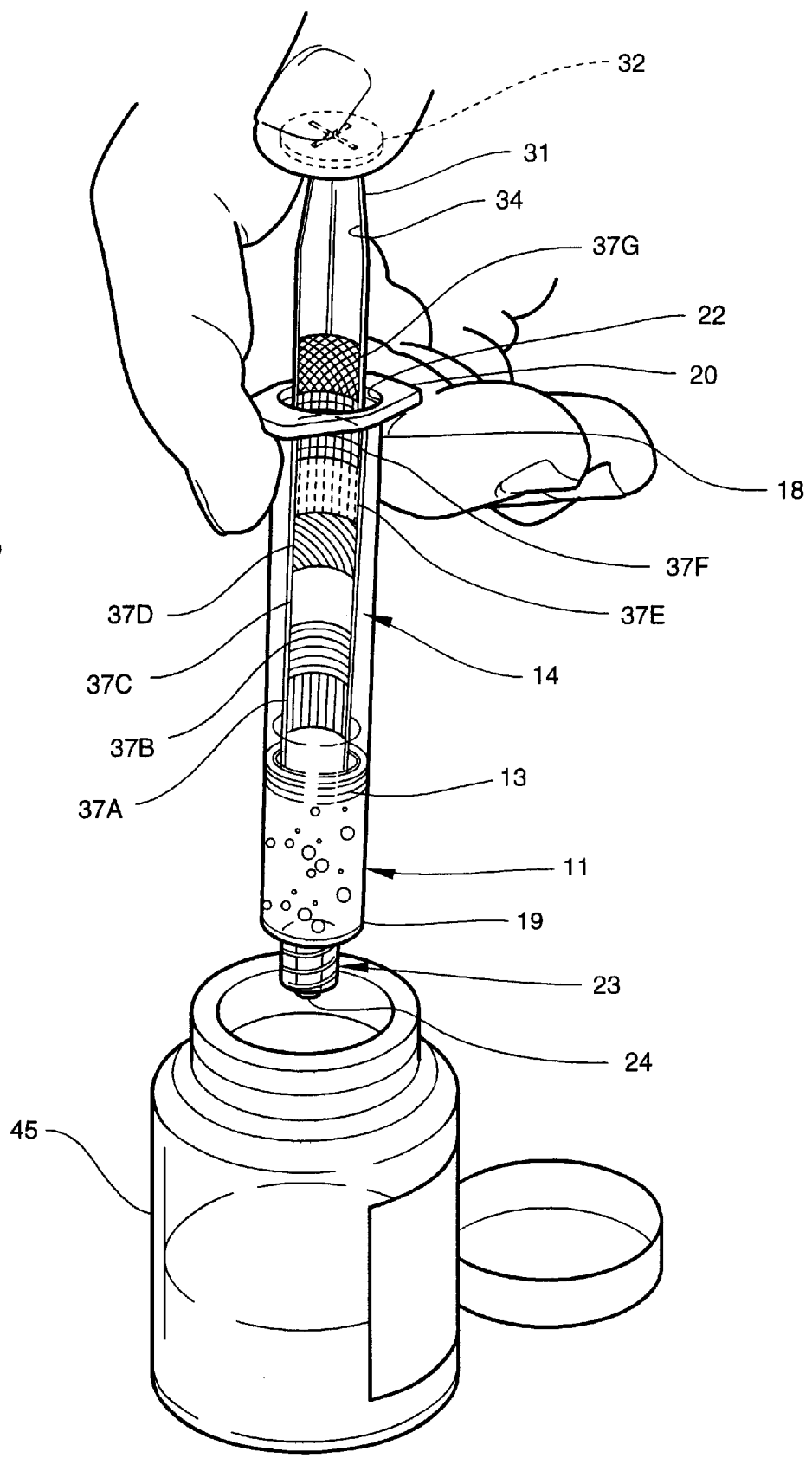
FIG. 5 is an environmental perspective view of the syringe according to FIG. 4.

Referring now to the drawings, a dosing syringe according to one preferred embodiment of the invention is illustrated in FIG. 1 and shown generally at reference numeral 10. The syringe 10 is shown prior to assembly and includes a barrel 11, a stopper 12, a plunger 13, and a dose measurement indicator 14. Although the barrel 11 may be any shape or size, the barrel 11 is preferably elongate and includes cylindrical interior and exterior sidewalls 15 and 16, respectively. As discussed more fully below with reference to FIG. 4, the interior sidewall 15 defines a chamber 17 within which the plunger 13 is received. The plunger 13 has an elongate shape complementary to that of the chamber 17.

Although the barrel 11 and plunger 13 may be formed from any suitable materials, the barrel 11 and plunger 13 are preferably formed from rigid plastic. Furthermore, the barrel 11 may be formed from transparent or opaque materials. However, the plunger 13 is formed from a transparent material for permitting the dose measurement insert 14 to be easily viewed when placed within the plunger 13.

Referring again to FIG. 1, the barrel 11 includes proximal and distal ends 18 and 19, respectively. A flange 20 is integrally formed with the proximal end 18 and defines an opening 22 that communicates with the chamber 17. A hub 23 is integrally formed with the distal end 19 of the barrel 11. The hub 23 includes a tip 24 through which a passageway 25 extends. As discussed in detail below with reference to FIG. 2, the passageway 25 is in fluid communication with the chamber 17 so that medicine or other fluid may be drawn into or dispensed from the chamber 17 using the tip 24. The tip 24 is concentrically positioned within a collar 26. Although any suitable collar may be used, the collar 26 may be a luer-type collar having threaded interior sidewalls 27 for receiving a needle if the medication is to be injected subcutaneously. See FIG. 5.

The plunger 14 includes interior and exterior sidewalls 28 and 29, respectively, which extend between respective first and second ends 30 and 31. As described more fully below with reference to FIG. 4, the stopper 12 is removably positioned on the first end 30. A flange 32 is integrally formed with the second end 31 of the plunger 13 and defines an opening 33. The opening 33 communicates with a chamber 34 that is defined by the interior sidewall 28.

As is shown in FIG. 1, the dose measurement indicator 14 includes proximal and distal ends 35 and 36, and has an elongate shape complementary to that of the shape defined by the interior sidewall 28 of the plunger 13. This permits the indicator 14 to be easily inserted through the opening 33 and positioned within the chamber 34. As is discussed more fully below with reference to FIGS. 6 through 6D, the dose measurement indicator 14 also includes a series of gradations 37A–37G positioned in a set order along the length of the indicator 16. Gradations 37A–37G represent a dosing range correlated to a range of values representing a preselected physiological characteristic shared by a given population of patients.

Although any suitable physiological characteristic may be used, one preferred characteristic is the weight of the patient. When weight is used, a series of dosages are correlated to respective weight-related values indicative of proper dosages of the medication for a given patient weight range. One of the gradations 37A–37G is then assigned to each of the respective weight-related values within the fixed sequence of gradations 37A–37G, so that the gradations 37A–37G collectively represent a dosage range for the medication being dispensed.

Referring again to FIG. 1, the proximal end 35 of the indicator 14 preferably has a tapered shape complementary to that of the interior sidewall 28 of the chamber 34. This prevents the proximal end 35 from being inserted into the chamber 34 in the wrong direction, which would result in reverse orientation of the gradations 37A–37G within the chamber 34, and subsequent miscalculation of dosages for patients.

Referring now to FIGS. 2 and 3, the dose measurement indicator 14 is retained in a stationary position within the chamber 34 by a detent ring 40 and a complementary pair of positioning detents 41A and 41B. The detent ring 40 is integrally formed with and extends around the circumference of the interior sidewall 28. As is shown in FIG. 3, positioning detents 41A and 41B are positioned on opposing side edges of the indicator 14 adjacent the proximal end 35. Each detent 41A and 41B has an axially-directed concave shape complementary to the axially-directed, convex shape of the detent ring 40. This permits the detent ring 40 to engage and interfere with the detents 41A and 41B as the indicator 14 is being positioned within the chamber 34, which in turn prevents the indicator 14 from falling from the plunger 13.

Referring now to FIG. 4, the manner in which the dose measurement indicator 14 is positioned within the chamber 34 of the plunger 13 is shown. The plunger 13 is shown in FIG. 4 positioned within the chamber 17 of the barrel 11, which gives the plunger 13 and barrel 11 a common, central axis and a symmetrical, longitudinal orientation. The plunger 13 is received within the barrel 11 by inserting the first end 30 of the plunger 13 through the opening 22 and into the chamber 17.

The dose measurement indicator 14 is inserted into the chamber 34 of the plunger 13 by aligning the distal end 36 of the indicator 14 with the opening 33, and then inserting the distal end 36 through the opening 33 and into the chamber 34. The indicator 14 is moved along the length of the chamber 34 in this manner until the detent ring 40 engages the detents 41A and 41B on the proximal end 35 of the indicator 14 in a manner identical to that described above with reference to FIGS. 2 and 3.

The opening 33 of the embodiment of the syringe 10 shown in FIG. 4 is cross-shaped, a shape formed from two integrally-formed slots that intersect one another at right angles. The slots extend along the length of the barrel 11 parallel to the longitudinal axis of the plunger 13, thereby giving the chamber 34 a cross-sectional shape like that of the opening 33. This unique shape permits the dose measurement indicator 14 to be repositioned and placed in alternative configurations within the chamber 34.

Referring again to FIG. 5, the manner in which the syringe 10 is used to measure a medically correct dose of fluid is shown. The plunger 13 is moved relative to the barrel 11 in a manner similar to that of a conventional syringe. The syringe 10 is shown in FIG. 5 in use with a dispensing container 45. In particular, upon being introduced through the opening 22 and into the chamber 17 of the barrel 11, the stopper 12 positioned on the first end 30 of the plunger 13 cooperates with the interior sidewall 15 of the barrel 11.

As is shown in FIG. 5, the dose measurement indicator 14 is marked with gradations 37A–54G. Although the gradations 37A–37G may be any series of suitable symbols, shapes or other indicia, the gradations 37A–37G on the embodiment of the dose measurement indicator shown in FIG. 5 are preferably a series of individual strips of distinct colors. Each color represents a correct dose of a medicine or other fluid correlated to a preselected physiological characteristic shared by a group of patients. This correlation is established in a manner identical to that discussed above with respect to FIG. 1. In particular, gradations 37A, 37B, 37C, 37D, 37E, 37F and 37G correspond to the colors red, blue, white, green, purple, yellow and orange, respectively.

Each of the colors corresponds to one of six different dosages of a specific medication or fluid. Assuming hypothetically that weight is the physiological characteristic used to determine the correct dosages, each color is correlated to one of six weight-related values that fall within a weight range for the group of patients. A correlation such as disclosed in the Broselow U.S. Pat. No. 4,713,888 is used, so that a given color is selected so that any dosage of medication for a patient of a given weight is always, for example, blue. Furthermore, the specific medications are grouped according to concentration. Thus, the gradations 37A–37G on a given indicator 14 may be used to dispense doses of any medication having a concentration to which the dosing values for the gradations 37A–37G correspond. Because the dosing values upon which the gradations 37A–37G are based are calculated for medicines sharing a specific concentration, the indicator 14 should not be used to dispense a dose of any medication having a concentration other than that which is specified for the indicator 14. Placing the gradations 37A–37G on the indicator 14 instead of the outside of the barrel 11 allows the syringe 10 to be used to dispense medications of varying concentrations. This is achieved by simply removing the dosing indicator 14 from the plunger 13 and replacing it with a different dosing indicator which corresponds to a group of medications which share a different concentration.

As is shown in FIG. 5, assuming hypothetically that a nurse was instructed to inject a pediatric patient with a dose of a specific medication, the prescribed dose would be represented by a single color. For example, if the patient based on his or her weight was classified as a "yellow", the nurse would select the dose measurement indicator 14 to which the medication corresponds, insert the indicator 14 into the plunger 14, and withdraw fluid from the container 45 and into the chamber 17 of the barrel 11 until the "yellow" gradation 37F is aligned with the flange 13. The conversions and variables normally associated with calculating a proper dose are replaced by the series of gradations 37A–37G on the indicator 14. Dosing becomes easy and reliable—even under difficult conditions.

Figure 6:
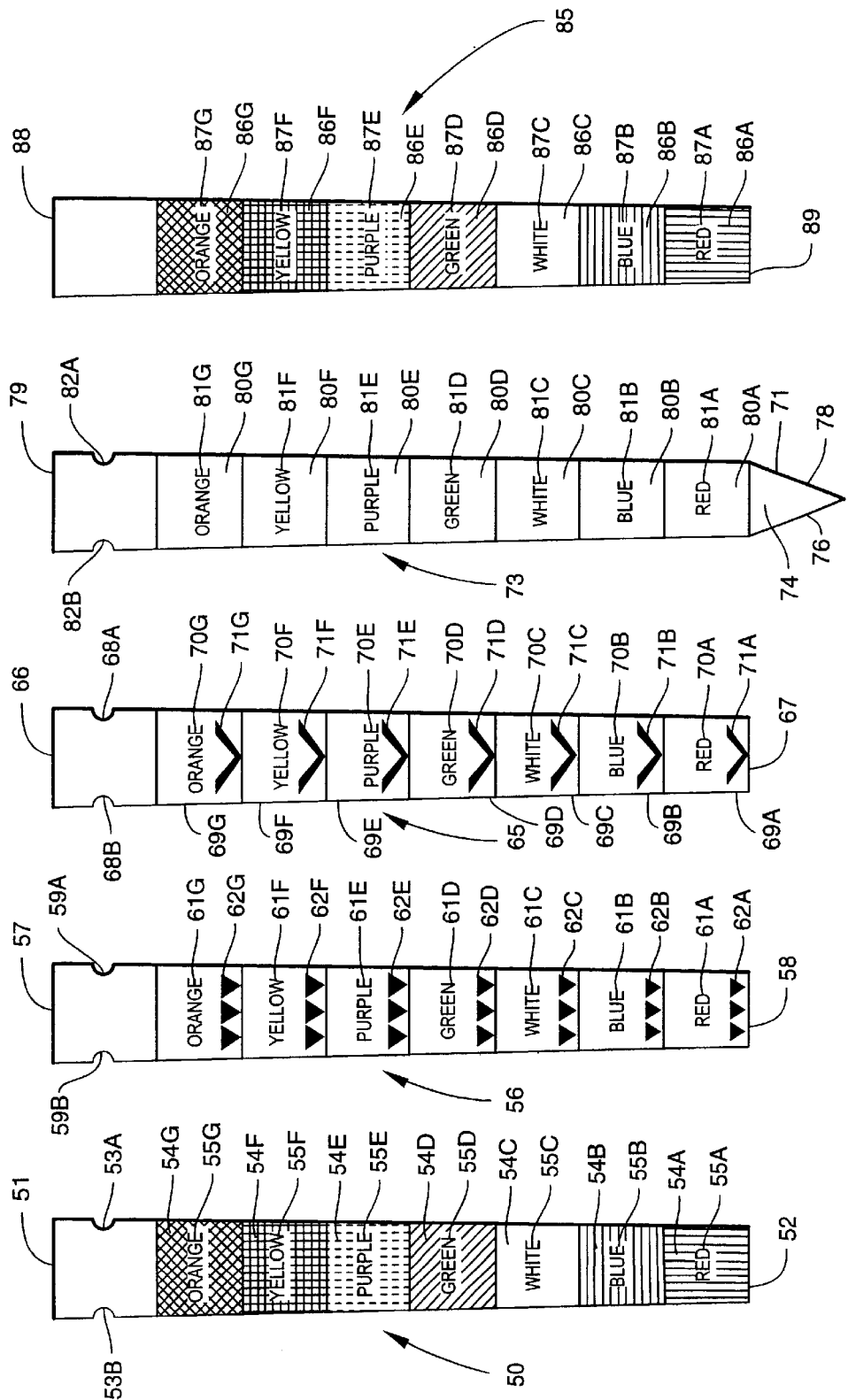
FIG. 6 is a front plan view of the dose measurement indicator used in the syringe according to FIG. 1.

Referring now to FIGS. 6 through 6D, alternative embodiments of the dose measurement indicator are shown. FIG. 6 illustrates a dose measurement indicator 50 having proximal and distal ends 51 and 52, respectively. A pair of positioning detents 53A and 53B are formed on opposing sides of the indicator 50 adjacent the proximal end 51. Each detent 53A and 53B has an axially-directed, concave shape for complementary engagement with a detent ring in a manner identical to that described above with respect to the detent ring 40. The indicator 50 also includes gradations 54A–54G which correspond to individual dosage values, but also a series of printed labels 55A–55G. Although each label 55A–55G may convey any suitable type of information regarding respective gradations 54A–54G, each label 55A–55G is preferably the name of the color that is used to mark the gradation 54A–54G upon which the label 55A–55G appears. Thus, gradations 54A, 54B, 54C, 54D, 54E, 54F and 54G, and respective labels 55A, 55B, 55C, 55D, 55E, 55F and 55G correspond to the colors red, blue, white, green, purple, yellow and orange, respectively. Labeling the gradations 54A–54G in this manner permits color-blind individuals to read the dose measurement indicator 50. The labels 55A through 55F may alternatively represent standard units of measurement.

Referring now to FIG. 6A, a dose measurement indicator according to another embodiment of the invention is shown generally at reference numeral 56. The indicator 56 includes proximal and distal ends 57 and 58, respectively, a pair of positioning detents 59A and 59B, gradations 60A–60G, and a series of printed labels 61A–61G identical in structure and function to those described above with reference to FIG. 6. The indicator 56 also includes rows of identically-shaped symbols 62A–62G. Each row of symbols 62A–62G mark the boundaries between the gradations 60A–60G, and thus serve as reference marks for a healthcare provider to rely upon when aligning the indicator 56 with the barrel 11 to determine the correct dosage associated with a given gradation 60A–60G.

With the exception of the use of chevrons 71A–71G instead of rows of symbols, the dose measurement indicator 65 shown in FIG. 6B is identical to the dose measurement indicator 56 shown in FIG. 6A. In particular, the indicator 65 has proximal and distal ends 66 and 67, respectively, a pair of positioning detents 68A and 68B, gradations 69A–69G, and labels 70A–70G which have structures and functions identical to like elements of the indicator 56 shown in FIG. 6A. The chevrons 71A–71G function identically to the rows of symbols 62A–62G on the indicator 56, and serve to clarify the location of the proper reference mark for each gradation 68A–68G and respective label 70A–70G associated therewith to make it easier for an individual dispensing medication to determine when the proper dose has been drawn into the chamber 17 of the barrel 11 of the syringe 10.

FIG. 6C illustrates a dose measurement indicator 73 that has a distal end 74 with side edges 76 and 77 which diverge to form a pointed tip 78. The shape of distal end 74 helps ensure that the indicator 72 remains stationary when placed within any one of the embodiments of the syringes of the present invention. The indicator 73 also includes a proximal and 79, gradations 80A–80G, labels 81A–81G, and positioning detents 82A and 82B, which are formed from the same materials and have the same functions as those of the indicator 65 shown in FIG. 6B.

Referring now to FIG. 6D, an alternative embodiment of the dose measurement indicator is illustrated and shown generally at reference numeral 85. Although the dose measurement indicator 85 may incorporate rows of symbols like the rows 62A–62G shown in FIG. 6A, or utilize chevrons like the chevrons 71A–71G of the indicator 65 shown in FIG. 6B, the dose measurement indicator 85 preferably has gradations 86A–86G and labels 87A–87G, and proximal and distal ends 88 and 89, respectively, like those of the indicator 50 shown in FIG. 6. However, unlike the indicator 50, the dose measurement indicator 80 lacks a pair of concave detents on the opposing side edges adjacent the proximal end 88. As is discussed in detail below with reference to FIGS. 9 through 11B, the indicator 85 is instead manipulated relative to its longitudinal axis to ensure that it is maintained in a stationary position inside the plunger.

Because each indicator 50, 56, 65, 73 and 85 is preferably formed from plastic, paper, lightweight cardboard or another similar material upon which the labels, symbols or other indicia are printed, the indicators 50, 56, 65, 73 and 85 may be printed prior to sale and delivery to the purchaser. Alternatively, blank indicators may be sold and delivered to the purchaser along with software specifically designed for use with conventional computers and which allows the purchaser to customize the appearance of the indicators with logos or other information and then print the same on the indicators along with the indicia, labels, and/or symbols.

Referring now to FIG. 7, another preferred embodiment of the syringe is illustrated and shown generally at reference numeral 90. The syringe 90 includes a barrel 92 formed from the same materials and including the same components as the barrel 11 of the syringe 10 shown in FIG. 1. The syringe 90 also includes a plunger 94 having cylindrical interior and exterior sidewalls 96 and 97, respectively, which extend between respective first and second ends 98 and 99. The second end 99 is preferably tapered, and includes a stopper 100 that is identical in structure and function to the stopper 12 shown in FIG. 1. The second end 99 of the plunger 94 includes a circular flange 101 through which an elongate slot 102 extends. The slot 102 communicates with a chamber 104 which is defined by the interior sidewall 96. The chamber 104 extends along the length of the plunger 94.

The syringe 90 also includes a dose measurement indicator 105 that has features and is formed from materials identical to the indicator 14 described above with reference to FIG. 6. However, unlike the indicator 14, which has a cupped cross-section extending perpendicular to its longitudinal axis when positioned within chamber 34, see FIG. 5, the dose measurement indicator 105 shown in FIG. 7 retains a planar cross-sectional shape when placed within the chamber 104.

Referring now to FIG. 7A, the indicator 105 is inserted through the slot 102. The indicator 105 is positioned within the chamber 104 so that the indicator 105 extends parallel to the slot 102. FIG. 7A shows the indicator 105 positioned in the chamber 104 after being inserted through the slot 102. The indicator 105 is maintained within the chamber 104 using a pair of concave positioning detents 107A and 107B positioned on opposing side edges of the indicator 105 adjacent the second end 99. A detent ring 108 having a cross-sectional, convex shape complementary to the concave shape of each detent 107A and 107B is integrally formed with and extends around the circumference of the interior sidewall 96 of the plunger 94 adjacent the second end 99. The detent ring 108 engages and interferes with the positioning detents 107A and 107B to prevent the indicator 105 from being displaced from its position within the chamber 104.

Although the plunger 94 utilizes an elongate slot 102, the which the indicator 105 passes before being positioned within the chamber 104, the plunger 94 may alternatively utilize a circular opening having a diameter equal to that of the diameter of the interior sidewall 96 of the plunger 94.

In addition to utilizing the complementary positioning detents 107A and 107B and the detent ring 108, the indicator 105 is also held in place within the chamber 104 by a pair of shoulders 110A and 110B which are formed at the point at which the interior sidewall 96 and opposing minor side edges 111A and 111B defining the slot 106A meet. The shoulders 110A and 110B engage the indicator 105, thereby preventing the indicator 105 from falling out of the chamber 104.

Referring now to FIG. 8, a dosing syringe according to an alternative embodiment of the invention is illustrated and shown generally at reference numeral 115. The syringe 115 includes a barrel 116 and complementary plunger 117 formed from the same materials and including the same components as the barrel 92 and plunger 94 of the syringe 90 described above with reference to FIGS. 7 through 7B. The plunger 117 has cylindrical interior and exterior sidewalls 118 and 119, respectively, and first and second ends 120 and 121. A stopper 122 is positioned on the first end 121. A circular flange 124 is integrally formed with the second end 121. A cross-shaped opening 125 is defined by and extends through the flange 124, and communicates with a chamber 126 that extends along the length of the plunger 117.

As is shown in FIG. 8, the syringe 115 also includes a dose measurement indicator 130. The indicator 130 preferably includes gradations 132A through 132G and labels 133A through 133G identical in function and appearance to the gradations 54A through 54G and labels 55A through 55G, respectively, of the indicator 50 described above with reference to FIG. 6. However, unlike the dose measurement indicator 50, the dose measurement indicator 130 lacks positioning detents and instead has smooth, opposing major side edges 134 and 135 between which respective upper and lower end edges 136 and 137 extend.

Referring now to FIG. 8A, the upper end edge 136 of the indicator 130 preferably has a width greater than the width of the opening 125. The width of upper end edge 136 is also preferably greater than the diameter of the chamber 126. This difference in widths causes the indicator 130 to have a cupped cross section which extends perpendicularly to the longitudinal axis of the chamber 126 at any given point along the length of the chamber 126. The cupped shape of the indicator 130 provides increased rigidity to the indicator 130, and stabilizes the position of the indicator 130 within the chamber 126 by creating increased resistance against the interior sidewall 96. The indicator 130 is also stabilized within the chamber 126 by a pair of shoulders 140A and 140B which are integrally formed with the interior sidewall 96. The shoulders 140A and 140B engage the upper end edge 136 of the indicator 130 to retain the indicator 130 within the chamber 126 of the plunger 117.

Referring now to FIG. 9, a dosing syringe according to another alternative embodiment of the invention is illustrated and shown generally at reference numeral 141. The syringe 141 has a barrel 142 formed from the same materials and including the same components as the barrel 12 discussed above with reference to FIGS. 1 through 5. The syringe 141 also includes an elongate plunger 143 that has cylindrical interior and exterior sidewalls 144 and 145, respectively. Sidewalls 144 and 145 extend between first and second ends 146 and 147, respectively. The first end 146 preferably has a tapered shape and a stopper 148 that is identical to the stopper 13 described above with reference to FIG. 5.

As is shown in FIG. 9, an annular flange 149 is integrally formed with the second end 147 of the plunger 143. A cross-shaped opening 150 is defined by and extends through the second end 146, and communicates with each of four separate channels 151A, 151B, 151C and 151D. Each of the channels 151A through 151D extends along the length of the plunger 142. A dose measurement indicator 152 is positioned within a preselected one of the channels 151A through 151D. The indicator 152 has gradations 154A through 154G and labels 155A through 155G that are identical in appearance and function to the gradations and labels of the indicator 50 described above with reference to FIG. 6. Like the indicator 130 shown in FIG. 8, the indicator 152 also lacks positioning detents.

Although the dose measurement indicator 152 may be positioned in any one of the channels 151A through 151D, the indicator 152 is shown in FIG. 9 positioned in channel 151A. A fold 156 extends along the longitudinal axis of the indicator 152, and stabilizes the indicator 152 within channel 151A. The indicator 152 is further stabilized and held in place within channel 151A by a shoulder 157 that is integrally formed with the interior sidewall 144 adjacent the second end 147. The shoulder 157 engages the indicator 152, which ensures that the indicator 152 will remain in a stationary position within the channel 151A.

Referring now to FIG. 10, a dosing syringe according to another preferred embodiment of the invention is illustrated and shown generally at reference numeral 160. The syringe 160 includes a barrel 161, and a plunger 162 is identical to the plunger 143 of the syringe 141 discussed above with reference to FIGS. 9 through 9B. In particular, the plunger 162 has cylindrical interior and exterior sidewalls 163 and 164, respectively, and respective first and second ends 165 and 166. A circular flange 167 is integrally formed with the second end 166 and defines a cross-shaped opening 168. The opening 168 extends through the flange 167 and communicates with four separate channels 169A–169D that are identical to the chambers 151A–151D of the plunger 143 shown in FIG. 9.

Referring again to FIG. 10, the syringe 160 also has a dose measurement indicator 170 with a cupped cross-sectional shape that extends perpendicularly to the longitudinal axis of the indicator 170 at any given point along the length thereof. By bending the indicator 170 in this manner, once the indicator 170 is placed within one of the channels 169A through 169D, each opposing major side edge 171 and 172 of the indicator 170 expands toward the walls defining the channel, which in turn causes the indicator 170 to stay securely positioned within the channel. FIGS. 10A and 10B show the indicator positioned within channel 169A. The indicia on the indicator 170 are aligned with a reference mark 161A on the barrel 161 to determine the volume of fluid retained within the barrel 161. Although the reference mark 161A is shown in FIG. 10 positioned on the outside of the barrel 161, the reference mark 161A may alternatively be positioned on the exterior sidewall 164 of the plunger 162.

Figure 11:
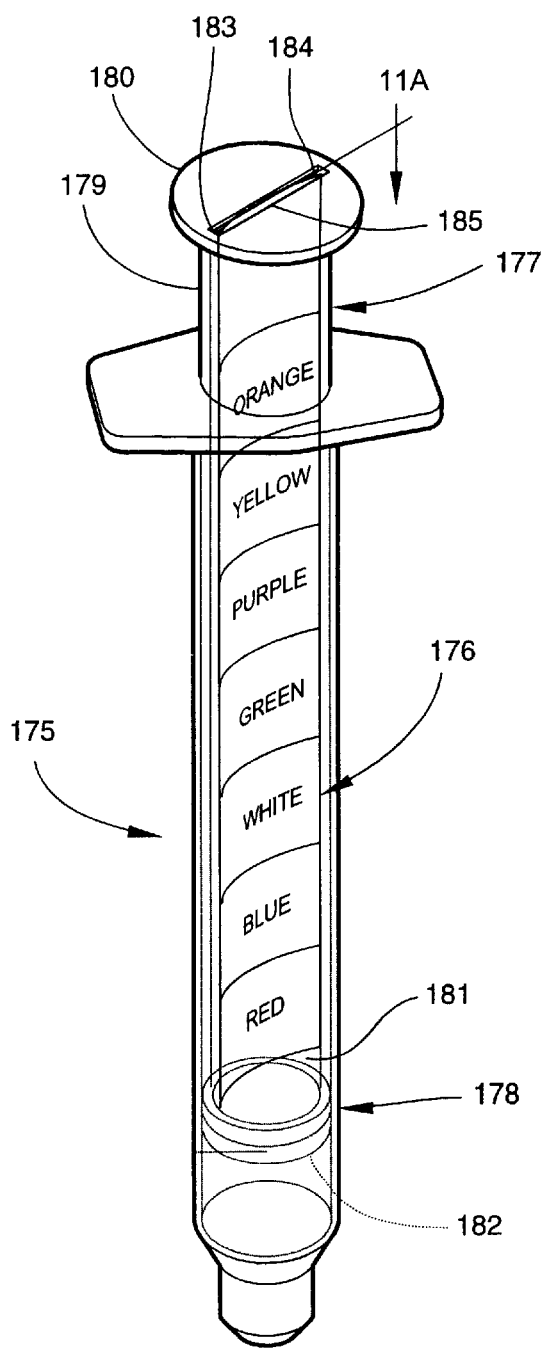
FIG. 11 is a perspective view of a dosing syringe according to an alternative embodiment of the invention.

Referring now to FIG. 11, a dosing syringe according to another preferred embodiment of the invention is illustrated and shown generally at reference numeral 175. The syringe 175 includes a dose measurement indicator 176 positioned within a plunger 177, which is in turn concentrically positioned within a barrel 178. The barrel 178 is identical in structure and function to the barrel 12 shown in FIG. 1. The indicator 176 is identical in structure and function to the indicator 85 shown in FIG. 6D.

Figure 11A:
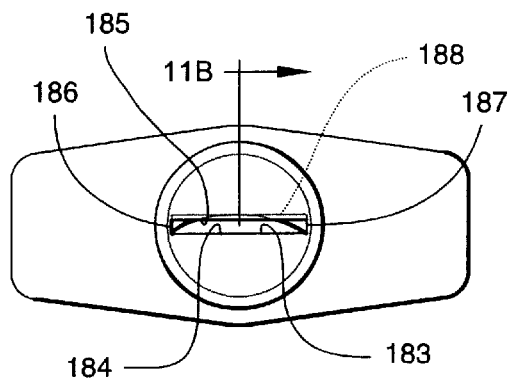
FIG. 11A is a top plan view of the dosing syringe taken along Line 11A of FIG. 11.
Figure 11B:
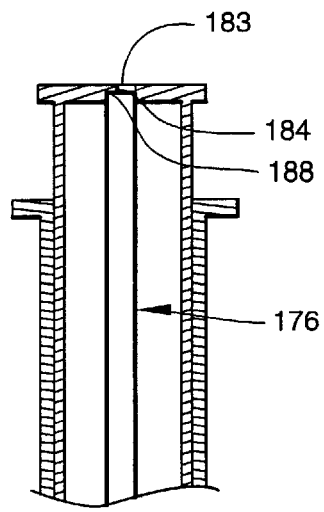
FIG. 11B is a partial cross-sectional side view of the dosing syringe taken along Line 11B of FIG. 11.

Referring again to FIG. 11, the plunger 177 of the syringe 175 includes an upper end 179 that is integrally formed with a flange 180, and a lower end 181 upon which a stopper 182 is positioned. An elongate slot 183 extends through the flange 180. The slot 183 is defined opposing major side edges 184 and 185, which are interconnected by spaced-apart, opposing minor side edges 186 and 187. As is shown in FIG. 11A, a shelf 188 is formed on and extends along the length of major side edge 184. As is shown in FIG. 11B, the shelf 188 engages the indicator 176, thereby maintaining the indicator 176 in a fixed position within the plunger 177.

Referring now to FIG. 12, a syringe according to another preferred embodiment of the invention is shown generally at reference numeral 190. The syringe 190 includes a barrel 192 and a plunger 194 formed from the same materials and including the same components as the barrel 92 and plunger 94 of the syringe 90 shown in FIGS. 7 through 7. However, unlike the syringe 90, the syringe 190 features a dose measurement indicator 196 that includes an elongate sleeve 200 within which a dose measurement insert 202 is positioned. As is shown in FIG. 12A, the sleeve 200 is preferably formed from a transparent, waterproof material such as plastic, and includes an interior compartment 204 which has a shape complementary to that of the dose measurement insert 202. The dose measurement insert may include any combination of the indicia, symbols, chevrons and/or colors shown in FIGS. 6 through 6D.

Positioning the insert 202 inside the plastic sleeve 200 not only protects the insert 202, but also permits the use of less expensive materials in the insert 202. In particular, while the dose measurement insert 202 may be formed from any suitable material, the insert 202 is preferably formed from paper. Using paper instead of plastic in the insert 202 reduces the cost of raw materials necessary to form the insert 202, and leads to significant cost savings during the printing process due to the decreased expense associated with printing on paper rather than on plastic.

Figure 13:
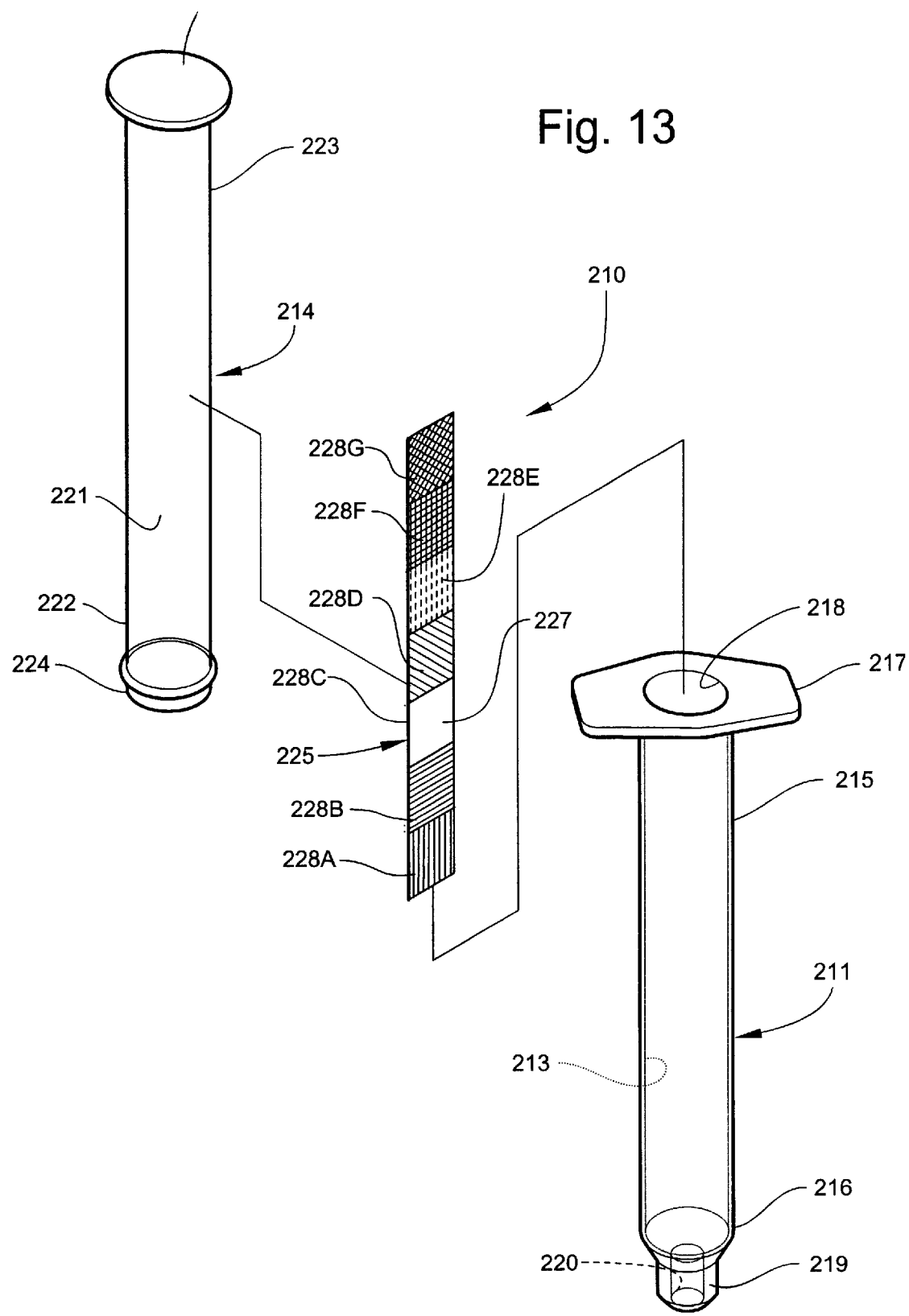
FIG. 13 is an exploded perspective view of a dosing syringe according to another preferred embodiment of the invention.

Referring now to FIG. 13, a dosing syringe according to another preferred embodiment of the invention is illustrated and shown generally at reference numeral 210. The syringe 210 includes a barrel 211 having a chamber 213 into which an elongate plunger 214 is received. The barrel 211 has proximal and distal ends 215 and 216, respectively. Proximal end 215 includes an integrally formed flange 217 defining an opening 218 that communicates with the chamber 213. The distal end 216 includes an integrally-formed tip 219 with a passageway 220 which is in fluid communication with the chamber 213. The plunger 214 has a cylindrical exterior sidewall 221 that extends between first and second ends 222 and 223, respectively. A stopper 224 is positioned on the first end 222 of the plunger 214.

Although the syringe 210 may be any suitable conventional syringe, the syringe 210 is preferably a syringe sold by Beckson, Dickinson and Company. Furthermore, while the barrel 211 may have any suitable tip, the tip 219 is preferably one like that which is sold by Beckson, Dickinson and Company under the tradename BD LUER LOK.

As is shown in FIG. 13, the syringe 210 also includes an elongate dose measurement indicator 225 having inner and outer surfaces 226 and 227, respectively. A series of gradations 228A–228G are printed in a set order on the outer surface 227. The gradations 228A–228G are printed along the length of the indicator 225, and represent a dosing range identical to the dosing range represented by the gradations 37A–37G included on the dose measurement indicator 14 shown in FIG. 1.

Figure 14:
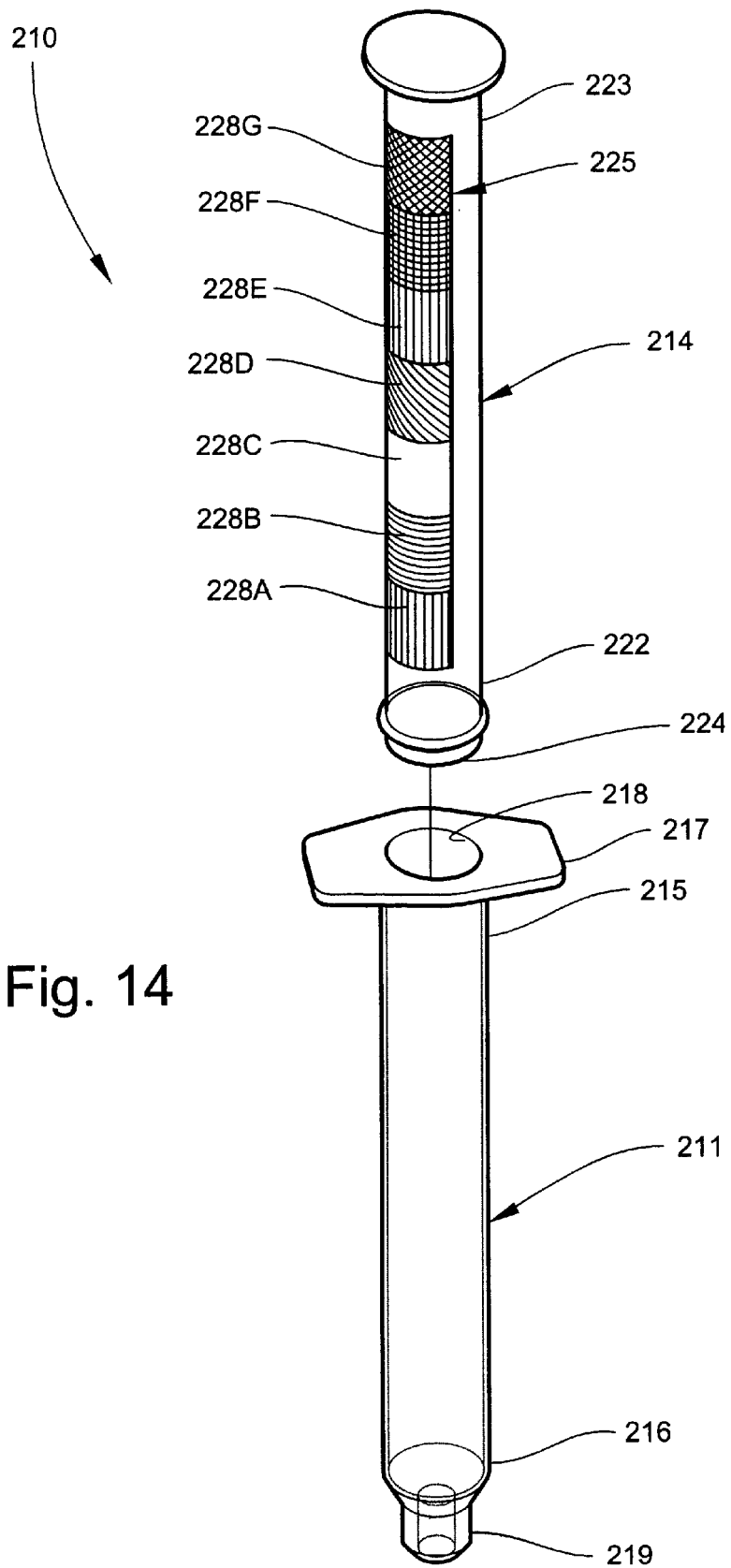
FIG. 14 is an exploded perspective view the dosing syringe shown in FIG. 13.

Unlike the dose measurement indicators shown in FIGS. 1 through 12C, each of which is designed to be inserted within a plunger, the dose measurement indicator 225 shown in FIG. 13 is designed to be attached to the exterior sidewall 221 of the plunger 214. In particular, the inner surface 226 of the indicator 225 is coated with a conventional adhesive, which permits the inner surface 226 to be positioned on and adhered in any position to the exterior sidewall 221. As is shown in FIG. 14, the adhesive-backed inner surface 226 is preferably attached directly to the exterior sidewall 221 so that the longitudinal axis of the indicator 225 extends parallel to the longitudinal axis of the plunger 214.

Providing a syringe 210 with an adhesive-backed indicator 225 capable of adhering to the exterior sidewall 221 of the plunger 214 in a manner similar to that of a conventional sticker or adhesive-backed decal eliminates the need to manufacture a plunger having a custom-shaped interior chamber, and simplifies the process of assembling the syringe. Because any suitable conventional syringe may be used, the medical provider or other user need only position the adhesive-backed indicator 225 in the proper position on the plunger and "stick" the indicator 225 in place, and the syringe 210 will be ready for use. Furthermore, indicators 225 may be sold separately for use on a pre-existing inventory of syringes, or sold in combination with conventional syringes as kits. In addition, the indicators 225 may be sold with the gradations 228A–228G preprinted on the outer surface 227, or without the gradations 228A–228A and in combination with a software program for permitting medical providers to design and print customized gradations, dose measurement indicia, logos and/or other suitable information on the indicators prior to attaching the indicators to the plungers.

Referring again to FIG. 13, although the gradations 228A–228G on the indicator 225 may be any series of suitable symbols, shapes or other indicia, the gradations 228A–228G are preferably a series of individual strips of distinct colors, each of which represents a correct dose of a medicine or other fluid correlated to a preselected physiological characteristic shared by a group of patients. Specifically, the gradations 228A, 228B, 228C, 228D, 228E, 228F and 228G correspond to the colors red, blue, white, green, purple, yellow and orange, respectively. Each of these colors corresponds to one of six different dosages of a specific medication or fluid, and is correlated to that specific dosage in a manner identical to that described above with reference to the gradations 37A–37G shown in FIG. 5. The gradations 228A–228G may alternatively be like any one or a combination of the series of gradations 54A–54G, 55A–55G, 61A–61G, 62A–62G and/or 71A–71G described above with reference to FIGS. 6 through 6B.

Figure 15:
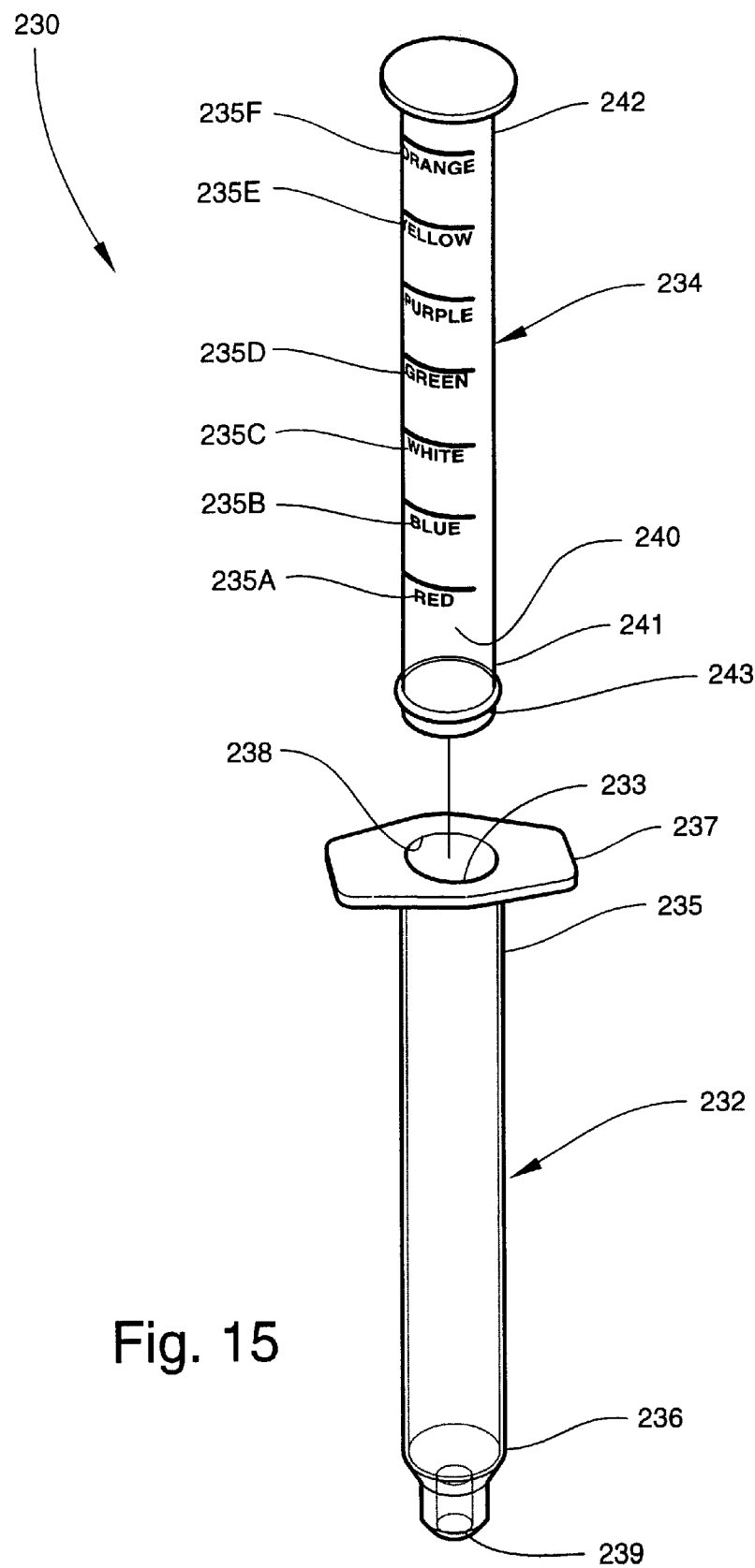
FIG. 15 is an exploded perspective view of a dosing syringe according to yet another preferred embodiment of the invention.

Referring now to FIG. 15, a dosing syringe according to yet another preferred embodiment of the invention is illustrated and shown generally at reference numeral 230. The syringe 230 includes a barrel 232 having a chamber 233 into which an elongate plunger 234 is received. The barrel 232 has proximal and distal ends 235 and 236, respectively. Proximal end 235 includes an integrally formed flange 237 defining an opening 238 that communicates with the chamber 233. A tip 239 is integrally formed with distal end 236. The plunger 234 has a cylindrical exterior sidewall 240 that extends between first and second ends 241 and 242, respectively. A stopper 243 is positioned on the first end 241.

Although the syringe 230 may be any suitable conventional syringe, like the syringe 210 shown in FIGS. 13 and 14, the syringe 230 is preferably one sold by Beckson, Dickinson and Company. The barrel 232 may include any suitable tip; however, the tip 239 is preferably that which is sold by Beckson, Dickinson and Company under the tradename BD LUER LOK.

As is shown in FIG. 15, the syringe 230 also includes a series of dose measurement indicia 235A through 235G that are printed directly onto the exterior sidewall 240 of the plunger 234. Printing the indicia 235A through 235G directly onto the exterior sidewall rather than on a separate dose measurement indicator which must then be inserted within the plunger or glued or otherwise attached to the outer surface thereof further simplifies the assembly and use of the syringe 230. In particular, because the indicia 235A through 235G are printed directly onto the exterior sidewall 235, the syringe 230 is assembled in a manner identical to that of any other conventional syringe. However, because the indicia 235A through 235G are located on the plunger rather than on the barrel, the indicia 235A through 235G may be read without having to withdraw the barrel 232 from the container from which medication is being withdrawn.

Each indicia 235A through 235G represents a correct dose of a medicine or other fluid correlated to a preselected physiological characteristic shared by a group of patients. This correlation is established in a manner identical to that of the gradations 37A through 37G discussed above with respect to FIG. 1. Although the indicia 235A through 235G consist of names of individual colors paired with reference lines, the indicia 235A through 235G may alternatively be like any one or a combination of the series of gradations 37A–37G, 54A–54G, 55A–55G, 61A–61G, 62A–62G and/or 71A–71G described above with reference to FIGS. 1 and 6 through 6B.

A color-coded medical dosing container is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. A dosing syringe, comprising:
   (a) a barrel defining a chamber therein for retaining fluid and including a dispensing port and a proximal opening communicating with said chamber for permitting fluid flow therethrough;
   (b) a plunger for being matingly received within the chamber through said proximal opening and axially moveable relative to said barrel for controlling fluid flow through said dispensing port, wherein the plunger comprises a first end for being matingly received through the proximal opening of the barrel, and a second end for manipulating axial movement of the plunger relative to the barrel, said plunger defining a compartment adapted for receiving a dosing indicator therein, said compartment being concentrically positioned within the plunger and communicating with a opening defined by and extending through said second end of the plunder; and
   (c) a dosing indicator carried by said plunger in said compartment and including indicia thereon collectively representing a dosing range of the fluid based upon a correlation between said indicia and a therapeutic treatment variable for a preselected group of patients, wherein said indicia cooperate with the plunger and barrel for measuring a medically correct dose of the fluid to be administered to a patient from the group.

2. A dosing syringe according to claim 1, wherein said dosing indicator is removably positioned within said plunger for permitting alternative uses of said syringe.

3. A dosing syringe according to claim 1, wherein the indicia comprise preselected strips of color arranged in a fixed sequence on the dosing indicator.

4. A dosing syringe according to claim 1, wherein each of the indicia comprise a respective one of a series of chevrons positioned in spaced-apart relation along the length of the dosing indicator.

5. A dosing syringe according to claim 1, wherein said indicia comprise preselected words arranged in a fixed sequence on the dosing indicator.

6. A dosing syringe according to claim 5, wherein each of said words corresponds to a preselected color for permitting a color-blind individual to use said syringe.

7. A dosing syringe according to claim 3, wherein each of said strips of color is overlaid by a respective one of a series of reference marks.

8. A dosing syringe according to claim 1, wherein the compartment comprises an elongate slot.

9. A dosing syringe according to claim 8, wherein said slot comprises two integrally formed, elongate segments positioned perpendicularly to one another and extending parallel to the longitudinal axis of the plunger.

10. A dosing syringe according to claim 9, wherein said segments intersect with each other to form an X-shaped cross section extending perpendicularly to the longitudinal axis of the plunger.

11. A dosing syringe according to claim 1, and including an alignment indicator carried by said barrel for being aligned with a preselected one of the indicia on said dosing indicator, thereby permitting the medically correct dose of the fluid to be measured prior to administering the dose to the patient.

12. A dosing syringe according to claim 8, wherein said dosing indicator comprises an elongate insert having a cross-sectional shape complementary to a cross-sectional segment of said slot.

13. A dosing syringe according to claim 1, wherein said interior compartment comprises a plurality of equally spaced channels defined by and extending along the length of the plunger, each of said channels adapted for receiving the dosing indicator therein.

14. A dosing syringe according to claim 13, wherein the dosing indicator comprises an elongate insert.

15. A dosing syringe according to claim 14, wherein said insert includes a fold extending parallel to the longitudinal axis thereof for maintaining the insert in a stationary position within a preselected one of the channels.

16. A dosing syringe according to claim 12, wherein the insert comprises a flexible strip for being placed in a bent position within a preselected one of the channels, thereby maintaining said strip in a stationary position with the channel.

17. A dosing syringe, comprising:
   (a) a barrel defining a chamber therein for retaining fluid and including a dispensing port and a proximal opening communicating with said chamber for permitting fluid flow therethrough;
   (b) a plunger for being matingly received within the chamber through said proximal opening and axially moveable relative to said barrel for controlling fluid flow through said dispensing port, wherein the plunger comprises a first end for being matingly received through the proximal opening of the barrel, and a second end for manipulating axial movement of the plunger relative to the barrel, said plunger defining a compartment adapted for receiving a dosing indicator therein, said compartment being concentrically positioned within the plunger and communicating with a opening defined by and extending through said second end of the plunger; and
   (c) a dosing indicator removably positioned within a said compartment defined by, said dosing indicator including indicia thereon collectively representing a preselected series of colors corresponding to a dosing range of the fluid based upon a correlation between said indicia and a therapeutic treatment variable for a preselected group of patients, wherein said indicia cooperate with the plunger and barrel for measuring a medically correct dose of the fluid to be administered to a patient from the group.

18. A method of measuring a medically correct dose of fluid for being administered to a patient, comprising the steps of:

(a) providing a dosing syringe including:
  (i) a barrel defining a chamber therein for retaining fluid and including a dispensing port and a proximal opening communicating with said chamber for permitting fluid flow therethrough;
  (ii) a plunger for being matingly received within the chamber through said proximal opening and axially moveable relative to said barrel for controlling fluid flow through said dispensing port, wherein the plunger comprises a first end for being matingly received through the proximal opening of the barrel, and a second end for manipulating axial movement of the plunger relative to the barrel, said plunger defining a compartment adapted for receiving a dosing indicator therein, said compartment being concentrically positioned within the plunger and communicating with a opening defined by and extending through said second end of the plunger; and
  (iii) a dosing indicator carried by said plunger and including indicia thereon collectively representing a dosing range of the fluid based upon a correlation between said indicia and a therapeutic treatment variable for a preselected group of patients, wherein said indicia cooperate with the plunger and barrel for measuring a medically correct dose of the fluid to be administered to a patient from the group;
(b) assigning a predetermined one of the indicia to the patient using the therapeutic treatment variable;
(b) providing a container of the fluid;
(c) immersing the dispensing end of the barrel into the fluid; and
(d) using the plunger to withdraw the fluid from the container and into the chamber until said predetermined indicia is aligned with a reference mark on the barrel, thereby indicating the medically correct dose of fluid is in the chamber.

* * * * *

UNITED STATES PATENT AND TRADEMARK OFFICE
CERTIFICATE OF CORRECTION

| | | |
|---|---|---|
| PATENT NO. | : 6,764,469 B2 | Page 1 of 1 |
| APPLICATION NO. | : 10/210992 | |
| DATED | : July 20, 2004 | |
| INVENTOR(S) | : James B. Broselow | |

It is certified that error appears in the above-identified patent and that said Letters Patent is hereby corrected as shown below:

Column 15, line 42, delete "plunder" and enter --plunger--.

Column 16, line 58, delete "within a said" and enter --within said--.

Column 16, line 59, delete "compartment defined by, said" and enter --compartment, said--.

Column 18, line 11, delete "(b) providing" and enter --(c) providing--.

Column 18, line 12, delete "(c) immersing" and enter --(d) immersing--.

Column 18, line 14, delete "(d) using" and enter --(e) using--.

Signed and Sealed this

Second Day of January, 2007

JON W. DUDAS
*Director of the United States Patent and Trademark Office*